(12) United States Patent
Channabasavaradhya et al.

(10) Patent No.: US 9,534,260 B2
(45) Date of Patent: Jan. 3, 2017

(54) MATERIALS AND METHODS FOR DETECTING THE ARYLOXYALKANOATE DIOXYGENASE GENE (AAD-12) CONTAINING EVENT PDAB4472-1606 IN PLANTS

(71) Applicant: DOW AGROSCIENCES LLC, Indianapolis, IN (US)

(72) Inventors: Chandra-Shekara A. Channabasavaradhya, Westfield, IN (US); Andrew Greenwald, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 50 days.

(21) Appl. No.: 13/654,697

(22) Filed: Oct. 18, 2012

(65) Prior Publication Data

US 2013/0095485 A1    Apr. 18, 2013

Related U.S. Application Data

(60) Provisional application No. 61/548,533, filed on Oct. 18, 2011.

(51) Int. Cl.
*C07H 21/04* (2006.01)
*C12Q 1/68* (2006.01)

(52) U.S. Cl.
CPC ......... *C12Q 1/6895* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,541,308 A * | 7/1996 | Hogan et al. ............... 536/23.1 |
| 6,689,880 B2 | 2/2004 | Chen et al. |
| 6,733,974 B1 | 5/2004 | Feazel |
| 6,740,488 B2 | 5/2004 | Rangwala et al. |
| 6,818,807 B2 | 11/2004 | Trolinder et al. |
| 6,825,400 B2 | 11/2004 | Behr et al. |
| 6,893,826 B1 | 5/2005 | Hillyard et al. |
| 6,900,014 B1 | 5/2005 | Weston et al. |
| 7,154,021 B2 * | 12/2006 | Hauge et al. ............... 800/267 |

FOREIGN PATENT DOCUMENTS

| | | | |
|---|---|---|---|
| WO | WO 2007/053482 | 5/2007 | |
| WO | WO 2011/066360 A1 * | 6/2011 | ............... C12Q 1/68 |
| WO | WO 2012033794 A2 * | 3/2012 | ............... A01H 1/06 |

OTHER PUBLICATIONS

Buck et al (Biotechniques (1999) 27(3):528-536).*
NEB Catalog (1998/1999, pp. 121, 284).*
Taverniers, I. et al. "Event-Specific Plasmid Standards and Real-Time PCR Methods for Transgenic Bt11, Bt176, and GA21 Maize and Transgenic GT73 Canola," *Journal of Agriculture and Food Chemistry*, Mar. 2005, pp. 3041-3052, vol. 53, No. 8.

* cited by examiner

*Primary Examiner* — Sarae Bausch
(74) *Attorney, Agent, or Firm* — Ronald S. Maciak; Saliwanchik, Lloyd & Eisenschenik

(57) ABSTRACT

This application provides materials and methods for the detection of the aad-12 gene and event pDAB4472-1606 in biological samples derived from plants.

13 Claims, 2 Drawing Sheets

SEQUENCE LISTING

<160> NUMBER OF SEQ ID NOS: 5

<210> SEQ ID NO 1
<211> LENGTH: 24
<212> TYPE: DNA
<213> ORGANISM: Artificial sequence
<220> FEATURE:
<223> OTHER INFORMATION: Forward primer

<400> SEQUENCE: 1
gccattaatt atagcggtgt ttgc                                    24

<210> SEQ ID NO 2

```
<211> LENGTH: 25
<212> TYPE: DNA
<213> ORGANISM: Artificial sequence
<220> FEATURE:
<223> OTHER INFORMATION: Reverse primer

<400> SEQUENCE: 2
cggttaggat ccggtgagta atatt                                          25

<210> SEQ ID NO 3
<211> LENGTH: 13
<212> TYPE: DNA
<213> ORGANISM: Artificial sequence
<220> FEATURE:
<223> OTHER INFORMATION: Probe

<400> SEQUENCE: 3
ccttgcaaaa ttc                                                        13

<210> SEQ ID NO 4
<211> LENGTH: 26
<212> TYPE: DNA
<213> ORGANISM: Artificial sequence
<220> FEATURE:
<223> OTHER INFORMATION: Reverse primer

<400> SEQUENCE: 4
gaatgaggct gcgtataaaa atacaa                                         26

<210> SEQ ID NO 5
<211> LENGTH: 18
<212> TYPE: DNA
<213> ORGANISM: Artificial sequence
<220> FEATURE:
<223> OTHER INFORMATION: Probe

<400> SEQUENCE: 5
tgtgttattg gcctcttg                                                   18
```

MATERIALS AND METHODS FOR DETECTING THE ARYLOXYALKANOATE DIOXYGENASE GENE (AAD-12) CONTAINING EVENT PDAB4472-1606 IN PLANTS

CROSS-REFERENCE TO RELATED APPLICATION

This application claims the benefit of U.S. Provisional Application Ser. No. 61/548,533, filed Oct. 18, 2011.

BACKGROUND OF THE INVENTION

Soybean is an important crop and is a primary food source in many areas of the world. The methods of biotechnology have been applied to soybean for improvement of agronomic traits and the quality of the product. Examples of agronomic traits introduced into soybean plants include herbicide resistance and insect resistance.

The aad-12 gene (originally from *Delftia acidovorans*) encodes the aryloxyalkanoate dioxygenase (AAD-12) protein. This gene confers tolerance to 2,4-dichlorophenoxyacetic acid, for example, and to pyridyloxyacetate herbicides. The aad-12 gene, itself, for introducing herbicide tolerance in plants was disclosed in WO 2007/053482.

The expression of heterologous or foreign genes (transgenes) in plants is influenced by where the foreign gene is inserted in the chromosome. This could, for example, be due to chromatin structure (e.g., heterochromatin) or the proximity of transcriptional regulation elements (e.g., enhancers) close to the integration site (Weising et al., *Ann. Rev. Genet* 22:421-477, 1988). Thus, the same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the gene construct introduced into the plant.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a transgene and/or genomic DNA of a particular plant in order to determine whether progeny of a sexual cross contain the transgene and/or genomic DNA of interest. In addition, a method for detecting the presence of the transgene and/or genomic DNA in a particular plant would be helpful when complying with regulations requiring the pre-market approval and labeling of foods derived from the recombinant crop plants.

It is possible to detect the presence of a transgene by any well known nucleic acid detection method. Examples include the polymerase chain reaction (PCR) or DNA hybridization using nucleic acid probes. These detection methods generally focus on frequently used genetic elements, such as promoters, terminators, marker genes, or other commonly used genetic elements. Such methods may not be useful for discriminating between different events, particularly those produced using the same DNA construct unless the sequence of chromosomal DNA adjacent to the inserted DNA ("flanking DNA") is known.

Event-specific PCR assays are, however useful in such a context and Taverniers et al. (*J. Agric. Food Chem.*, 53: 3041-3052, 2005) disclose an event-specific tracing system for transgenic maize lines Bt11, Bt176, and GA21 and for canola event GT73. In Taverniers et al., event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

BRIEF SUMMARY OF THE INVENTION

The present invention relates to the AAD-12 soybean (*Glycine max*) event designated pDAB4472-1606 having representative seed deposited with American Type Culture Collection (ATCC) with Accession No. PTA-11028, and progeny derived thereof. The subject invention provides methods of identifying soybean plants having genomic DNA (gDNA) containing this event.

Thus, one aspect of the invention provides assays for detecting the presence of the subject event in a biological sample (from soybeans, for example). The assays can be based on the DNA sequence of the recombinant construct inserted into the soybean genome. Kits and conditions useful in conducting the assays are also provided.

The subject invention also relates to nucleic acid sequences useful for the cloning and analysis of the DNA sequences of a related to an aad-12 insert. Certain embodiments of this aspect of the invention provide event-specific primers for detecting an aad-12 insert and PCR amplicons generated with these event-specific primer sets. Thus, these and other related procedures can be used to uniquely identify soybean lines containing an aad-12 insert (event pDAB4472-1606).

DETAILED DESCRIPTION OF THE INVENTION

Figure 1:
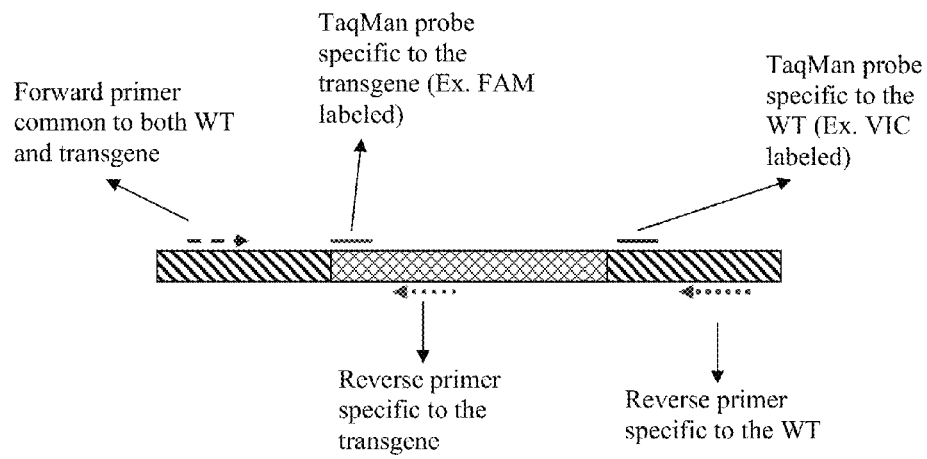
FIG. 1. Scheme of a zygosity assay design. When the length of the transgene is large (>5 kb), the Taq polymerase cannot amplify the large fragment with common and wild type specific primers. The result is that only the common and target specific primers amplify a DNA fragment, thereby only the transgene is detected.

One aspect of the invention provides assays for detecting the presence of transgenic soybean event pDAB4472-1606 in plant lines containing (comprising) these events as well as the cloning and analysis of the DNA sequences of the aad12 insert. Plant lines containing event pDAB4472-1606 can be detected using primer and probe sequences disclosed herein.

The subject invention also provides assays and materials for detecting the presence of event pDAB4472-1606 in order to determine whether progeny of a sexual cross between two soybean plants, at least one of which contains the event of interest (event pDAB4472-1606). In addition, a method for detecting the event is helpful, for example, for complying with regulations requiring the pre-market approval and labeling of foods derived from recombinant crop plants. As would be apparent to those skilled in the art, it is possible to detect the presence of event pDAB4472-1606 by any well-known nucleic acid detection method such as polymerase chain reaction (PCR) or DNA hybridization using nucleic acid probes.

The introduction and integration of a transgene into a plant genome involves random events (hence the name "event" for a given insertion that is expressed) and, for many transformation techniques, such as *Agrobacterium* transformation, "gene gun" transformation and WHISKERS, it is unpredictable where a transgene will become inserted in the genome of a plant.

At least 2500 seeds of a soybean line comprising event pDAB4472-1606 have been deposited and made available to the public without restriction (but subject to patent rights), with the American Type Culture Collection (ATCC), 10801 University Boulevard, Manassas, Va., 20110. The deposit has been designated as ATCC Deposit No. PTA-11028. 100 packets (25 seeds per packet) of Glycine max seeds (AAD-12 Soybean Event pDAB4472-1606) were deposited on behalf of Dow AgroSciences LLC on Jun. 10, 2010. The deposit was tested on Jun. 29, 2010, and on that date, the seeds were viable. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

Definitions and examples are provided herein to help describe the present invention and to guide those of ordinary skill in the art to practice the invention. Unless otherwise noted, terms are to be understood according to conventional usage by those of ordinary skill in the relevant art.

A "biological sample" can comprise any organic material derived from soybean cells or tissue, including stems, roots, leaves, flowers or flower parts, seed or seed pods, and the like, that contains a detectable amount of a nucleotide sequence corresponding to such organic material. A biological sample derived from soybean containing event pDAB4472-1606 comprises the transgene/genome insertion regions corresponding to event pDAB4472-1606.

A "probe" is an isolated nucleic acid to which is attached a conventional detectable label or reporter molecule, e.g., a radioactive isotope, fluorophore, ligand, chemiluminescent agent, or enzyme. Such a probe is complementary to a strand of a target nucleic acid, in the case of the present invention, to a strand of genomic DNA containing event pDAB4472-1606 whether from a soybean plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic acid amplification methods.

Probes and primers are generally 11 to 30 nucleotides or more in length. In certain instances, probes and primers can have lengths of more than 30 nucleotides. Regardless of size, probes and primers can hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

As used herein, the term "progeny" denotes the offspring of any generation of a parent plant which comprises (or contains) aad-12 soybean event pDAB4472-1606.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As discussed above, one aspect of the invention relates to event identification. Related PCR primers and amplicons are included in the invention. According to the subject invention, analytic PCR methods using amplicons that span inserted DNA can be used to detect or identify commercialized transgenic soybean varieties or lines derived from proprietary transgenic soybean lines containing event pDAB4472-1606. Thus, various embodiments of the invention provide primers comprising SEQ ID NO: 1, SEQ ID NO: 2, SEQ ID NO: 4 or various combinations thereof and probes comprising SEQ ID NO: 3, SEQ ID NO: 5 or both SEQ ID NOs: 3 and 5.

Detection techniques disclosed herein are useful, in conjunction with plant breeding, to identify progeny plants containing event pDAB4472-1606, after a parent plant containing said event is crossed with another plant line in an effort to impart one or more additional traits of interest in the progeny. These PCR analysis methods benefit soybean breeding programs as well as quality control, especially for commercialized transgenic soybean seeds and can also benefit product registration and product stewardship.

Thus, another aspect of the invention provides processes for making crosses using a plant containing event pDAB4472-1606 as at least one parent (e.g., an $F_1$ hybrid plant having as one or both parents a plant containing event pDAB4472-1606) and analyzing the resultant progeny plants using primers and/or probes as disclosed herein. A herbicide-tolerant soybean plant of the subject invention can be bred by first sexually crossing a first parental soybean plant consisting of a soybean plant grown from seed of the line referred to herein or from any soybean plant containing event pDAB4472-1606, and a second parental soybean plant, thereby producing a plurality of first progeny plants; then selecting a first progeny plant that is resistant to a herbicide (or that possesses at least one of the events of the subject invention); selfing the first progeny plant, thereby producing a plurality of second progeny plants; and then selecting second progeny possessing event pDAB4472-1606 using assays, primers and/or probes described herein.

One skilled in the art will also recognize that primers and probes can be designed to hybridize, under a range of standard hybridization and/or PCR conditions, including conditions where the primer or probe is not perfectly complementary to the exemplified sequence. That is, some degree of mismatch can be tolerated. For an approximately 20 nucleotide primer, for example, typically one or two or so nucleotides do not need to hybridize with the opposite strand if the mismatched base is internal or on the end of the primer that is opposite the amplicon. Various appropriate hybridization conditions are provided below. Furthermore, synthetic nucleotide analogs, such as inosine, can also be used in probes. Peptide nucleic acid (PNA) probes, as well as DNA and RNA probes, can also be used.

In some embodiments of the invention, compositions are provided for detecting the presence of event pDAB4472-1606. These compositions comprise event-specific primers, such SEQ ID NO: 2, and primers that hybridize with DNA common to the wild-type genome of plants that do not contain event pDAB4472-1606 (SEQ ID NO: 1 and/or SEQ ID NO: 4). PCR analysis demonstrated that soybean lines containing event pDAB4472-1606 can be identified by analysis of the PCR amplicons generated with these event-specific primer sets (SEQ ID NO: 2). These and other related procedures can be used to uniquely identify these soybean lines containing event pDAB4472-1606. Thus, PCR amplicons derived from such primers and can be used to identify soybean lines containing event pDAB4472-1606 and form another embodiment of the disclosed invention.

This invention also includes methods of detecting the presence of DNA, in a sample, that comprises plant material containing event pDAB4472-1606. Such methods can comprise: (a) contacting the sample comprising DNA with a primer set that, when used in a nucleic acid amplification reaction with DNA, produces an amplicon that identifies event pDAB4472-1606 within the sample (e.g., SEQ ID NOs: 1 and 2); (b) performing a nucleic acid amplification reaction, thereby producing the amplicon; and (c) detecting the amplicon.

Further detection methods of the subject invention include a method of detecting the presence of a DNA, in a sample, corresponding to event pDAB4472-1606, wherein said method comprises: (a) contacting the sample comprising DNA with a probe that hybridizes under stringent hybridization conditions with DNA from plant material containing event pDAB4472-1606 and which does not hybridize under the stringent hybridization conditions with plant material from a control soybean plant (a plant that does not contain event pDAB4472-1606, also referred to as non-event-of-interest DNA); (b) subjecting the sample and probe to stringent hybridization conditions; and (c) detecting hybridization of the probe to the DNA.

According to another aspect of the invention, methods of determining the zygosity of progeny of a cross with plants containing event pDAB4472-1606 is provided. These methods can comprise contacting a sample comprising soybean DNA with a primer set disclosed herein. These primers, when used in a nucleic-acid amplification reaction with genomic DNA from a plant containing event pDAB4472-1606, produces a first amplicon that identifies a plant as containing event pDAB4472-1606. These methods further comprise performing a nucleic acid amplification reaction, thereby producing the first amplicon; detecting the first amplicon; and contacting the sample comprising soybean DNA with another primer set that, when used in a nucleic-acid amplification reaction with genomic DNA from soybean plants, produces a second amplicon comprising the native soybean genomic DNA homologous to the soybean genomic region. The method can also further comprise performing a nucleic acid amplification reaction to produce a second amplicon, detection of the second amplicon and comparing the first and second amplicons in a sample. The presence of both amplicons in a sample indicates that the sample is heterozygous for event pDAB4472-1606.

A "probe" is an isolated nucleic acid molecule to which is attached a conventional detectable label or reporter molecule (such as a radioactive isotope, ligand, chemiluminescent agent, or enzyme). Probes disclosed herein include SEQ ID NOs: 3 and/or 5. Probes according to the present invention include not only deoxyribonucleic or ribonucleic acids but also polyamides and other probe materials that bind specifically to a target DNA sequence and can be used to detect the presence of that target DNA sequence. Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989.

Depending on the application, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses. In a particular embodiment, a primer or probe disclosed herein will specifically hybridize to genomic DNA containing event pDAB4472-1606. The hybridization of the probe or primer to DNA containing event pDAB4472-1606 can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon. The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains event pDAB4472-1606 within its genomic DNA, DNA extracted from a soybean plant tissue sample may be subjected to nucleic acid amplification method using a primer pair disclosed herein to produce an amplicon that identifies the presence of event pDAB4472-1606. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of the present invention. The sequence of the heterologous transgene DNA insert from a subject soybean event can be verified (and corrected if necessary) by amplifying such sequences from the event using primers derived from the sequences provided herein followed by standard DNA sequencing of the PCR amplicon or of the cloned DNA. The amplicon produced by these methods may be detected by a plurality of techniques. Agarose gel electrophoresis and staining with ethidium bromide is a common well known method of detecting DNA amplicons.

TAQMAN (PE Applied Biosystems, Foster City, Calif.) is a method of detecting and quantifying the presence of a DNA sequence. Briefly, a FRET oligonucleotide probe is designed that hybridizes with a sequence of interest (e.g., the aad12 gene or a gene native to the soybean genome). The FRET probe and PCR primers are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the sequence of interest due to successful amplification and hybridization. Molecular beacons have also been described for use in sequence detection and can be used in accordance with the subject invention.

Thus, according to another aspect of the invention, methods of detecting the presence of DNA corresponding to the event pDAB4472-1606 in a biological sample are provided. Such methods comprise: (a) contacting the biological sample with a primer set that, when used in a nucleic acid amplification reaction with genomic DNA obtained from one or more soybean plant(s) containing event pDAB4472-1606, produces an amplicon that is identifies the plant as containing event pDAB4472-1606; (b) performing a nucleic acid amplification reaction, thereby producing the amplicon; and (c) detecting the amplicon wherein detection of said amplicon is indicative of presence of the DNA corresponding to event pDAB4472-1606.

According to another aspect of the invention, methods of detecting the presence of a DNA corresponding to event pDAB4472-1606 in a biological sample are provided. These, methods comprise: (a) contacting the biological sample with a probe that hybridizes under stringent hybridization conditions with genomic DNA from a soybean plant containing event pDAB4472-1606 and does not hybridize under the stringent hybridization conditions with a control soybean plant; (b) subjecting the biological sample and probe to stringent hybridization conditions; and (c) detecting hybridization of the probe to the DNA containing event pDAB4472-1606, wherein detection of such hybridization in indicative of presence of the DNA corresponding to event pDAB4472-1606 within the genome of the plant. Preferably, the probe is SEQ ID NO:3.

Yet another aspect of the invention is a method of determining zygosity of the progeny of soybean plants containing event pDAB4472-1606. The method comprises (a) contacting a biological sample with a primer pair of SEQ ID NOs: 1 and 2, that when used in a nucleic acid amplification reaction with genomic DNA from a biological sample containing genomic DNA from a biological sample from a soybean plant containing event pDAB4472-1606, produces a first amplicon that identifies the presence of the aad-12 gene within the genomic DNA of the biological sample; (b) performing a nucleic acid amplification reaction; (c) detecting a first amplicon produced (using SEQ ID NO: 3 as a labeled probe); (d) contacting the same sample with the primer pair SEQ ID NOs: 1 and 4, that when used in a nucleic acid amplification reaction with a biological sample containing genomic DNA from soybean plants produces an amplicon from the combination of primers that identifies wild-type soybean genomic DNA homologous to the soybean genomic region of a transgene insertion identified as event pDAB4472-1606; (e) performing a nucleic acid amplification reaction, and (f) detecting a second amplicon produced (using SEQ ID NO: 5 as a detection probe); wherein: (a) detection of both amplicons indicates that the soybean sample is heterozygous for event pDAB4472-1606; (b) detection of only said first amplicon (identifying the presence of the aad-12 gene) indicates the biological sample is homozygous for event pDAB4472-1606; and (c) detection of only said second amplicon is indicative of the absence of event pDAB4472-1606 within the biological sample. The detection of the amplicons can be performed using labeled probes (e.g., SEQ ID NOs: 3 and 5). As discussed above, probes can be labeled with a conventional detectable label or reporter molecule, e.g., a radioactive isotope, fluorescent label, ligand, chemiluminescent agent, or enzyme. In some embodiments, the probes are labeled with fluorescent labels that allow one to distinguish between an amplicon containing the aad-12 gene and an amplicon that does not contain the aad-12 gene (e.g., fluorophore/quencher combinations such as 6-carboxyfluorescein (FAM) or tetrachlorofluorescin (TET) in combination with quenchers such as tetramethylrhodamine, (TAMRA) or dihydrocyclopyrroloindole tripeptide (MGB).

In another embodiment of the invention, an aad-12 gene specific assay, such as that described in co-pending U.S. Provisional patent application Ser. No. 61/548,543, filed on Oct. 18, 2011; MATERIALS AND METHODS FOR DETECTING THE ARYLOXYALKANOATE DIOXYGENASE GENE (AAD-12) IN PLANTS; Inventors: Chandra Channabasavaradhya and Andrew Greenwald; hereby incorporated by reference in its entirety), can be paired with event specific PCR, such as that described and claimed herein. This embodiment can be used to determine if there are mixed aad-12 events in the same plant and whether the event detected by the event specific assay is hemizygous or homozygous. In this embodiment a gene specific assay is performed and the gene copy number is estimated based on fluorescent signal intensities produced by the gene specific assay. This is then compared to that of a known event specific zygosity assay, such as those disclosed herein. If the aad-12 gene copy number estimation is of similar intensity to that estimated by the event specific assay, then a sample is deemed to have only the intended aad-12 event. If the copy number estimated by the gene specific assay is more than that estimated by the event specific assay, then the sample under study is deemed to have additional aad-12 gene copies in addition to the intended event and hence indicates potential contamination of other aad-12 gene events. This scheme can also be used to detect contaminating events that bear identical gene elements other than the aad-12 gene such as promoter or selectable marker sequences or any other identical sequences common to all the events. The latter approach can be applicable to determine zygosity and/or contamination of transgenic events of various traits but having similar elements in the gene cassette.

Kits for the detection of event pDAB4472-1606 in soybean plants and biological samples derived therefrom are provided which use primers selected from SEQ ID NOs: 1, 2, and/or 4 and probes selected from SEQ ID NOs: 3 and 5. An amplicon produced using said kit is identifies a biological sample as containing event pDAB4472-1606 when the amplicon hybridizes with a probe comprising SEQ ID NO: 3. The kit can be provided as a means for specifically detecting the presence of event pDAB4472-1606 within soybean plants (or biological samples derived therefrom) or the kit can be provided as a means for detecting a multiplicity of different transgenic events from any number of different biological samples. In the latter case, i.e., a kit for detecting a multiplicity of different transgenic events, the kit may provide probes or primers in the form of a micro array, or any sort of array which provides the user of said kit with the ability to distinguish differences between transgenic and non-transgenic samples, zygosity of transgenic events, and even the presence or absence of events, whether approved or unapproved for commercialization. Detection or scoring of the presence or absence of certain events using such kits can be by fluorometric, colorimetric, isotopic, or chemiluminescent means.

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

EXAMPLES

Figure 2:
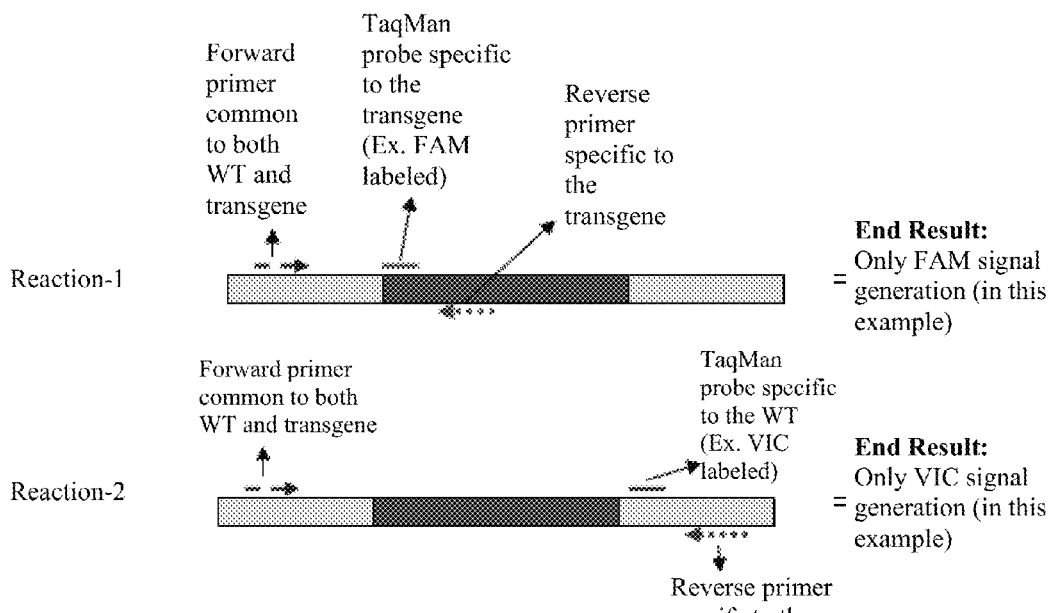
FIG. 2. The assay involves performing a standard zygosity protocol as two separate reactions which are outlined below: Reaction 1 (Control Reaction)—Common primer, Transgene specific primer, and a transgene specific probe (FAM), and; Reaction 2 (Zygosity Test Reaction)—Common primer, Wild type specific primer, and a wild type specific probe (VIC).
Figure 3:
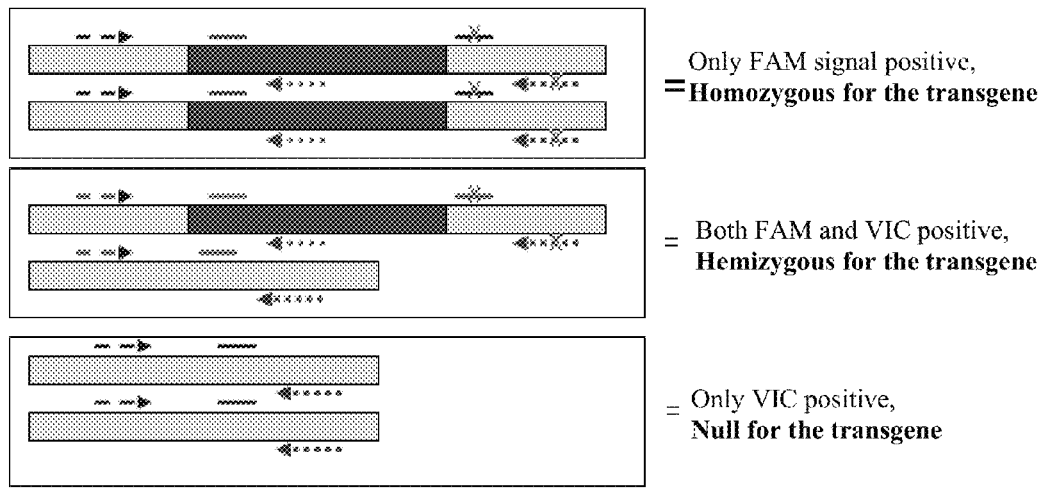
FIG. 3. Standard zygosity assay calls.

An event specific TAQMAN ASSAY® was developed to detect the presence of an MGB probe for event pDAB4472-1606 in soybean and to determine zygosity status of plants in breeding populations. To develop a gene specific assay, specific Taqman primers and probes were designed according to the DNA sequences located at the 5' insertion site of event pDAB4472-1606. For specific detection of event pDAB4472-1606 in soybean, a 209 by DNA fragment was amplified using two event specific primers. The amplification of this PCR product was measured by a target-specific MGB probe synthesized by Applied Biosystems containing the FAM reporter at its 5'end. Specificity of this Taqman detection method for event pDAB4472-1606 in soybean was tested against event pDAB4472-1606 soybean plants of varying levels of zygosity and non-transgenic soybean. These reactions were completed in a duplex format with wild type primer sequences which amplified a 181 bp fragment which spans the insertion locus of non-transgenic soybean (FIGS. 1, 2 and 3).

gDNA Isolation

Genomic DNA was extracted using the Qiagen DNeasy 96 Plant Kit. Fresh soybean leaf discs, 4 per sample, were used for gDNA extraction using a modified Qiagen DNeasy 96 Plant Kit protocol. The gDNA was quantified with the Pico Green method according to vendor's instructions (Molecular Probes, Eugene, Oreg.). Samples were diluted with DNase-free water resulting in a concentration of 10 ng/µL for the purpose of this study.

Taqman Assay and Results

Specific Taqman primers and probes were designed for the detection of event pDAB4472-1606 in soybean via a Taqman assay. These reagents can be used with the conditions listed below to detect event pDAB4472-1606 within soybean. Table 1 lists the primer and probe sequences that were developed specifically for the detection of event pDAB4472-1606 in soybean.

TABLE 1

PCR Primers and Probes

| Name | Description | 5' to 3' sequence |
|---|---|---|
| Event Target Reaction | | |
| D-Sb1606-Cm-F | Common Forward Primer | SEQ ID NO: 1 GCCATTAATTATAGCGGTGTTTGC |
| D-SB1606-Ev-R | Reverse Primer | SEQ ID NO: 2 CGGTTAGGATCCGGTGAGTAATATT |
| D-SB1606-FM | Probe | SEQ ID NO: 3 FAM-CCTTGCAAAATTC-MGB |
| Reference System Reaction | | |
| D-SB1606-Wt-R | Reverse Primer | SEQ ID NO: 4 GAATGAGGCTGCGTATAAAAATACAA |
| D-SB1606-VC | Probe | SEQ ID NO: 5 VIC-TGTGTTATTGGCCTCTTG-MGB |

The multiplex PCR conditions for amplification listed in Table 2. The cocktail was pipetted into a 96-well plate and was amplified using the following conditions: i) 50° C. for 2 min., ii) 95° C. for 10 min., iii) 95° C. for 15 sec, iv) 60° C. for 60 sec, iv) repeat step iii-iv for 35 cycles, v) 4° C. hold. The Real time PCR was carried out on the BIO-RAD ICYCLER™ and ABI Gene Amp PCR System 9700 thermocylers. Data analysis was based on measurement of the cycle threshold (Ct), which is the PCR cycle number when the fluorescence measurement reaches a set value. Ct value was calculated automatically by iCycler software.

Wild type control samples, which do not contain event pDAB4472-1606, will only produce Relative Fluorescence Unit (RFU) readings for the VIC flurophore. Samples which are hemizygous or homozygous for event pDAB4472-1606 genomic DNA will result in RFU readings for the FAM fluophore. These RFU readings are 0.5-1.0 units higher than that of the negative background control. Samples yielding no PCR products for the transgene or flanking genomic alleles may be the result of DNA that is not of adequate quality or quantity, and is an indication that the assay should be repeated. On completion of PCR and fluorescence readings, a distribution graph can be generated wherein samples which are hemizygous, homozygous or null are clustered as data points allowing the cut-off points to be visually determined.

TABLE 2

Reaction Mixture for event pDAB4472-1606 specific Taqman in soybean.

| Component | Concentration | Volume |
|---|---|---|
| TaqMan ® Genotyping Master Mix | 2x | 2 µl |
| Primer Mix | 20 µM | 0.1 µl |
| D-Sb1606-VC (100 µM) | 20 µM | 0.04 µl |
| D-Sb1606-FM (100 µM) | 20 µM | 0.04 µl |
| PVP | 0.05% | 0.82 µl |
| Sample DNA | | 1 µl |
| Total volume | | 4 µl |

Figure 4:
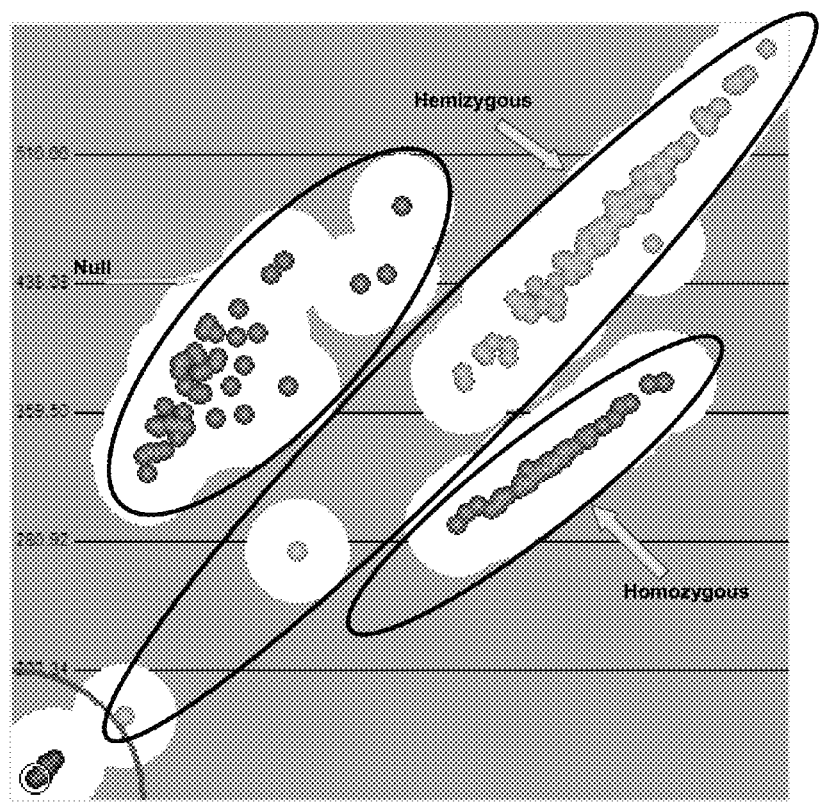
FIG. 4. Distribution graph between sample numbers based on Relative Fluorescence Units (RFU). Null, homozygous and hemizygous spot groupings are indicated within the circled areas.

The Taqman detection method for event pDAB4472-1606 in soybean was tested against homozygous, hemizygous, and null samples in duplex format with soybean wildtype specific primers as a reference gene. This assay specifically detected the event pDAB4472-1606 in soybean and did not produce or amplify any false-positive results from the controls (see FIG. 4). The event specific primers and probes can be used for the detection of event pDAB4472-1606 in soybean and these conditions and reagents are applicable for zygosity assays.

We claim:

1. A composition comprising a combination of primers and probes, said combination of primers comprising SEQ ID NO: 1, SEQ ID NO: 2 and SEQ ID NO: 4 and said combination of probes comprising SEQ ID NO: 3 and SEQ ID NO: 5, said probes having a detectable label attached to said probe, said detectable label being selected from a radioactive isotope, fluorescent label, chemiluminescent agent or enzyme and said probes and primers consisting of the recited SEQ ID NOS.

2. The composition according to claim 1, wherein said detectable label is a radioactive isotope.

3. The composition according to claim 1, wherein said detectable label is a fluorescent label.

4. The composition according to claim 1, wherein said detectable label is a chemiluminescent agent.

5. A kit comprising a container and a composition within said container, said composition comprising a combination of probes and primers, said combination of primers comprising SEQ ID NO: 1, SEQ ID NO: 2 and SEQ ID NO: 4 and said combination of probes comprising SEQ ID NO: 3 and SEQ ID NO: 5, said probes having a detectable label attached to said probes, said detectable label being selected from a radioactive isotope, fluorescent label, chemiluminescent agent or enzyme and said probes and primers consisting of the recited SEQ ID NOS.

6. The kit according to claim 5, wherein said detectable label is a radioactive isotope.

7. The kit according to claim 5, wherein said detectable label is a fluorescent label.

8. A composition comprising a thermostable polymerase and a combination of nucleic acid sequences, the combination of nucleic acids comprising a detectable label selected from a radioactive isotope, florescent label, chemiluminescent agent or enzyme, and the combination of nucleic acid sequences consisting of the recited SEQ ID NO and being selected from the following combinations of sequences:
   a) SEQ ID NO: 2 and SEQ ID NO: 4;
   b) SEQ ID NO: 2 and SEQ ID NO: 5;
   c) SEQ ID NO: 3 and SEQ ID NO: 4; or
   d) SEQ ID NO: 3 and SEQ ED NO: 5.

9. The composition according to claim 8, wherein the detectable label is attached to SEQ ID NO 3 and SEQ ID NO 5.

10. The composition according to claim 8, wherein said combination of nucleic acid sequences is SEQ ID NOs: 2 and 4.

11. The composition according to claim 8, wherein said combination of nucleic acid sequences is SEQ ID NOs: 2 and 5.

12. The composition according to claim 8, wherein said combination of nucleic acid sequences is SEQ ID NOs: 3 and 4.

13. The composition according to claim 8, wherein said combination of nucleic acid sequences is SEQ ID NOs: 3 and 5.

\* \* \* \* \*

UNITED STATES PATENT AND TRADEMARK OFFICE
CERTIFICATE OF CORRECTION

PATENT NO. : 9,534,260 B2
APPLICATION NO. : 13/654697
DATED : January 3, 2017
INVENTOR(S) : Chandra-Shekara A. Channabasavaradhya and Andrew Greenwald It is certified that error appears in the above-identified patent and that said Letters Patent is hereby corrected as shown below:

In the Specification

Column 10,
Line 65, "209 by DNA" should read --209 bp DNA--.

Column 14,
Line 55, "SEQ ED NO: 5." should read --SEQ ID NO: 5.--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*